United States Patent
Murase

(10) Patent No.: US 9,460,903 B2
(45) Date of Patent: Oct. 4, 2016

(54) GLYCOPEPTIDE ANALYZER

(71) Applicant: SHIMADZU CORPORATION, Kyoto-shi, Kyoto (JP)

(72) Inventor: Masaki Murase, Nagoya (JP)

(73) Assignee: SHIMADZU CORPORATION, Kyoto (JP)

( * ) Notice: Subject to any disclaimer, the term of this patent is extended or adjusted under 35 U.S.C. 154(b) by 164 days.

(21) Appl. No.: 14/553,311

(22) Filed: Nov. 25, 2014

(65) Prior Publication Data

US 2015/0144783 A1 May 28, 2015

(30) Foreign Application Priority Data

Nov. 27, 2013 (JP) ................................. 2013-244499

(51) Int. Cl.
*H01J 49/40* (2006.01)
*H01J 49/16* (2006.01)
*H01J 49/02* (2006.01)
(Continued)

(52) U.S. Cl.
CPC .......... *H01J 49/009* (2013.01); *G01N 33/6842* (2013.01); *G01N 33/6851* (2013.01); *H01J 49/40* (2013.01); *H01J 49/42* (2013.01); *C12Q1/6872* (2013.01); *C12Q 2565/627* (2013.01); *C40B 20/08* (2013.01); *Y10T 436/24* (2015.01)

(58) Field of Classification Search
CPC .... H01J 49/4225; H01J 49/40; H01J 49/009; H01J 49/004; Y10T 436/24; G01N 33/6848; G01N 33/6803; G01N 33/6851; C12Q 2565/627; C12Q 1/6872; C40B 20/08
USPC ........................................................ 250/287
See application file for complete search history.

(56) References Cited

U.S. PATENT DOCUMENTS 7,473,892 B2 * 1/2009 Sano .................. G01N 33/6848
250/281
9,159,539 B2 * 10/2015 Larson ................ H01J 49/0045
(Continued)

FOREIGN PATENT DOCUMENTS

JP 2011-175897 A 9/2011

OTHER PUBLICATIONS

O Masaki Murase, et al., "Data-dependent acquisition system for N-linked glycopeptides using MALDI-DIT-TOF MS", a poster session No. PWe-058 at 19th International Mass Spectrometry Conference (IMSC), 2012, 1 page.
(Continued)

Primary Examiner — Jack Berman
Assistant Examiner — Kevin Chung
(74) Attorney, Agent, or Firm — Sughrue Mion, PLLC

(57) ABSTRACT

The same sample S is analyzed using an ion-trap (IT) mass spectrometer section 11 in which ions are captured in an ion trap before mass spectrometry and a time-of-flight (TOF) mass spectrometer section 12 in which ions generated from the sample are directly subjected to mass spectrometry. A mass spectrum creator 21 creates an IT mass spectrum and a TOF mass spectrum from the measured results. A glycopeptide detector 23 detects fragment ion peaks related to neutral loss of sugars from the IT mass spectrum as well as peaks corresponding to intact molecular ions from the TOF mass spectrum, and furthermore, detects peaks common to the two spectra as glycopeptide ions. A quantitative analyzer 24 determines relative quantities of glycoforms of the glycopeptide based on the TOF mass spectrum. A structural analyzer 25 analyzes the structure of the glycopeptide using the result of an MS" analysis of the sample S.

4 Claims, 5 Drawing Sheets

(51) Int. Cl.
*H01J 49/00* (2006.01)
*G01N 33/68* (2006.01)
*H01J 49/42* (2006.01)
*C12Q 1/68* (2006.01)
*C40B 20/08* (2006.01)

(56) References Cited

U.S. PATENT DOCUMENTS

| | | | |
|---|---|---|---|
| 2002/0037532 A1* | 3/2002 | Regnier | G01N 33/6803 435/7.1 |
| 2009/0250604 A1* | 10/2009 | Amano | G01N 33/5308 250/282 |
| 2011/0095176 A1* | 4/2011 | Castro-Perez | H01J 49/0031 250/282 |
| 2011/0312522 A1* | 12/2011 | Tempst | G01N 33/57484 506/9 |

OTHER PUBLICATIONS

Yoshinao Wada, et al., "Comparison of the methods for profiling glycoprotein glycans—HUPO Human Disease Glycomics/Proteome Initiative multi-institutional study", Glycobiology, 2007, pp. 411-422, vol. 17, No. 4.

* cited by examiner

GLYCOPEPTIDE ANALYZER

TECHNICAL FIELD

The present invention relates to a glycopeptide analyzer for analyzing the structure of a glycosylated protein or peptide by mass spectrometry, and more specifically, to a glycopeptide analyzer for the determination of relative quantities or the structural analysis of glycoforms having different sugar-chain structures.

BACKGROUND ART

It is said that more than half of the proteins which compose living organisms are glycosylated. Glycosylation plays important roles in the structural and functional control of proteins. Recent studies have also revealed that some kinds of diseases (e.g. immunity disorder) are associated with abnormalities in sugar-chain structures or saccharification. With such a technical background, structural analysis of glycoproteins and glycopeptides has been significantly important in bioscience, medical treatment, drug development and various other fields.

Due to the rapid progress in the matrix-assisted laser desorption/ionization ion-trap mass spectrometer (MALDI-IT MS) or matrix-assisted laser desorption/ionization ion-trap time-of-flight mass spectrometer (MALDI-IT-TOF MS) in recent years, accompanied by the advancement in the analytical techniques using such devices, it has become possible to analyze the structure of glycopeptides or similar complexes of molecules having different physical and/or chemical properties (e.g. sugar chain and peptide in the case of glycopeptide). For example, Non Patent Literature 1 discloses an automatic glycopeptide analyzer system using a MALDI-IT-TOF MS. This system is capable of analyzing the structure of a glycopeptide by combining various techniques, such as the $MS^2$ and $MS^3$ analyses, the deduction of sugar-chain structures using de novo sequencing, and the identification of peptides by database search (the deduction of amino-acid sequences).

A MALDI linear TOF MS, which uses no ion trap and allows ions generated from a sample to be directly sent into a flight space, is suitable for a measurement which requires high sensitivity, high quantitative determination accuracy and high reproducibility, since the system has the characteristic that, even if post source decay (the phenomenon in which ions generated from a sample decay in the middle of their flight) occurs, the ions resulting from the decay reach the ion detector without being lost. Another advantage of the MALDI linear TOF MS is that it can perform an analysis with high throughput and over a wide range of mass-to-charge ratios since it does not capture ions with an ion trap. To utilize those advantages, MALDI linear TOF MSs are often used for quantitative analysis of glycopeptides.

For example, Non Patent Literature 2 discloses a technique for determining the quantities of glycoforms in a glycoprotein using a MALDI linear TOF MS. The quantity determination of glycoforms according to this literature is performed as follows:

(1) A glycoprotein is purified.
(2) The glycopeptide is broken into glycopeptides by enzymatic digestion.
(3) The glycopeptides are condensed.
(4) By a reverse-phase liquid chromatograph, the glycopeptides are separated into groups each of which consists of glycopeptides having the same glycosylation site.
(5) The glycoform mixtures separated according to their glycosylation sites are individually subjected to mass spectrometry ($MS^1$ analysis) using a MALDI linear TOF-MS.
(6) The relative quantities of the glycoforms having different sugar-chain structures corresponding to their glycosylation sites are determined using the intensities of the peaks on mass spectra obtained through the $MS^1$ analysis.

CITATION LIST

Patent Literature

Patent Literature 1: JP 2011-175897 A

NON PATENT LITERATURE

Non Patent Literature 1: Murase et al., "Data-dependent acquisition system for N-linked glycopeptides using MALDI-DIT-TOF MS", a poster session No. PWe-058 at 19th International Mass Spectrometry Conference (IMSC), 2012, an abstract of which is contained in the PDF file accessible through the "ABSTRACTS" link in the "Scientific Program" section on the IMSC 2012 website.

Non Patent Literature 2: Wada et al., "Comparison of the methods for profiling glycoprotein glycans—HUPO Human Disease Glycomics/Proteome Initiative multi-institutional study", Glycobiology, 2007, Vol. 17(4), pp. 411-422

SUMMARY OF INVENTION

Technical Problem

In the previously described analysis of glycopeptides using a MALDI-IT MS or MALDI-IT-TOF MS, fragment ions of a glycopeptide ion from which sugar has been partially or entirely dissociated is easily produced in the process of capturing ions in the ion trap. Therefore, if the sample contains a mixture of protein isoforms (glycoforms) which merely differ from each other in sugar-chain structure, it is impossible to determine whether the detected ion is an ion of a glycopeptide which has been contained in the sample from the start or a fragment ion which has resulted from an unintended dissociation of sugar in the aforementioned way. Thus, in an analysis using a MALDI-IT MS or MALDI-IT-TOF MS, if a glycoform mixture is contained in the sample, a fragment ion which is not present in the original sample may be mistaken for an ion which has been present in the sample from the start. To avoid this situation, it is necessary to perform a pre-treatment for purifying glycoforms to a high degree of purity. This task is extremely complex and cumbersome.

In the case of the MALDI linear TOF MS, which has conventionally been used for quantitative analysis of glycoforms, it is impossible to determine whether an ion peak located on an $MS^1$ spectrum has originated from the glycopeptide of interest or another molecule. If a MALDI-TOF/TOF MS employing a reflectron time-of-flight mass separator combined with a high-energy collision induced dissociation cell is available (e.g. "AXIMA Performance", a product manufactured by Shimadzu Corporation), it is possible to perform an $MS^2$ analysis and determine whether or not a precursor ion used in the $MS^2$ analysis is a glycopeptide ion. However, it is impossible to previously narrow down the precursor ions for the $MS^2$ analysis to only glycopeptide ions before the $MS^2$ analysis is actually performed. Therefore, it is inevitable to perform useless $MS^2$ analyses for ions that should actually be excluded, and a considerable amount of time will be required for the $MS^2$ analysis. Another problem is that the amount of collision energy used in the $MS^2$ analysis by TOF/TOF MS is so large that a considerable amount of secondary fragmentation occurs, which lowers the reliability of identification of the glycosylation site. Still another drawback is that no sufficient structural information can be obtained from an $MS^2$ spectrum of a glycopeptide whose molecular weight exceeds 5000. Thus, in terms of the performance in the structural analysis of glycopeptides, MALDI-TOF/TOF MS is inferior to MALDI-IT MS or MALDI-IT-TOF MS using an ion trap.

The present invention has been developed in view of the previously described problems. Its objective is to provide a glycopeptide analyzer capable of efficiently performing quantitative determination and/or structural analysis of glycoforms with high accuracy, without performing any cumbersome pre-treatment.

Solution to Problem

The present invention aimed at solving the previously described problem is a glycopeptide analyzer for performing an analysis on a glycoform mixture of a glycoprotein or glycopeptide, including:

a) an ion-trap mass spectrometer section having an ion trap capable of temporarily capturing ions generated from a sample and fragmenting the captured ions, the ion-trap mass spectrometer section being configured to separate the ions according to their mass to charge ratios by the ion trap or another mass separator and to detect the separated ions;

b) a time-of-flight mass spectrometer section for introducing ions generated from a sample into a flight space, for separating the ions according to their mass-to-charge ratios within the flight space, and for detecting the separated ions;

c) a glycopeptide detector section for detecting peaks related to the dissociation of a portion or the entirety of the glycan on a first $MS^1$ spectrum created based on the result of a measurement by the ion-trap mass spectrometer section, for detecting molecular ion peaks on a second $MS^1$ spectrum created based on the result of a measurement by the time-of-flight mass spectrometer section, and for finding glycopeptide ions from common peaks located on both $MS^1$ spectra;

d) a quantitative analyzer section for determining, for the glycopeptide ion detected by the glycopeptide detector section, a relative quantity of a glycoform using a relative peak intensity on the second $MS^2$ spectrum; and e) a structural analyzer section for performing, for the glycopeptide ion detected by the glycopeptide detector section, a structural analysis of a glycoform using, at least, the result of an $MS^n$ analysis (where n is an integer equal to or greater than two) performed by the ion-trap mass spectrometer section.

Examples of the "ion-trap mass spectrometer section" include an ion-trap mass spectrometer in which the mass separation is performed in the ion trap itself, an ion-trap time-of-flight mass spectrometer in which ions ejected from an ion trap are separated by a time-of-flight mass separator and detected, as well as a Fourier transform mass spectrometer having the function of capturing ions in a manner substantially identical to an ion trap. On the other hand, the "time-of-flight mass spectrometer section" is typically a time-of-flight mass spectrometer having a linear or reflectron flight space, although a TOF/TOF system capable of high-energy collision induced dissociation may also be used. In any of these mass spectrometer sections, the ion source is typically a MALDI ion source but is not limited to this type. For example, it is possible to use an ion source employing a surface assisted laser desorption ionization (SALDI) method.

In the glycopeptide analyzer according to the present invention, the ion-trap mass spectrometer section and the time-of-flight mass spectrometer section may be provided in a completely separated form, or they may be constructed as a hybrid system in which their elements are partially shared. One example of such a system is described in Patent Literature 1, in which an ion source, a time-of-flight mass separator and an ion detector are shared, and an ion trap is provided between the ion source and the time-of-flight mass separator. In the first operation mode, the inner space of the ion trap serves as a portion of the flight space, and the ions generated by the ion source and accelerated are allowed to pass through the ion trap and enter the true flight space formed by the time-of-flight mass spectrometer, to be subjected to mass spectrometry. In the second operation mode, the ions generated by the ion source are temporarily captured in the ion trap, in which the selection and/or fragmentation of the ions is performed as needed. Subsequently, the ions are simultaneously ejected from the ion trap and introduced into the flight space of the time-of-flight mass separator, to be subjected to mass spectrometry. In this system, the two modes of mass spectrometry using the ion-trap mass spectrometer section and the time-of-flight mass spectrometer section can be performed in a time-shared manner.

In the glycopeptide analyzer according to the present invention, samples containing the same glycopeptide are subjected to the two modes of mass spectrometry using the ion-trap mass spectrometer section and the time-of-flight mass spectrometer section, respectively, and an $MS^1$ spectrum, i.e. a normal mass spectrum, is created in each mode of mass spectrometry. Although these mass spectra correspond to the same sample, each mass spectrum has unique characteristics in the kinds of peaks appearing on it. In the ion-trap mass spectrometer section, as already noted, a portion or the entirety of the glycan is easily dissociated as a neutral loss in the ion-capturing process by the ion trap, so that a considerable number of peaks formed by neutral loss are observed on the first $MS^1$ spectrum. Accordingly, the glycopeptide detector section analyzes the first $MS^1$ spectrum by de novo sequencing or other data processing to detect each peak which is likely to be an ion from which sugar has been dissociated as a neutral loss. By contrast, in the time-of-flight mass spectrometer section, it is often the case that molecular ions are observed in intact forms. Accordingly, the glycopeptide detector section detects each significant peak on the second $MS^1$ spectrum which satisfies a certain condition (e.g. each peak whose signal intensity exceeds a threshold), on the assumption that such a peak corresponds to an "intact ion", i.e. an ion originating from an intact molecule.

It should be noted that the sample may possibly contain non-glycosylated peptides or other molecules in addition to the glycoforms of the target glycopeptide. The peaks originating from those other molecular ions also appear on the second $MS^1$ spectrum. On the other hand, the peaks observed on the first $MS^1$ spectrum should always include peaks originating from the glycoforms of the target glycopeptide which are present in the sample from the start. Accordingly, the glycopeptide detector section examines the commonality in the mass-to-charge ratio between the peaks related to neutral loss of sugars detected in the first $MS^1$ spectrum and the peaks on the second $MS^1$ spectrum detected as such peaks that have probably originated from intact ions. In this examination, for example, any pair of peaks located on the two $MS^1$ spectra with the mass-to-charge-ratio difference being within an acceptable error tolerance is identified as a peak originating from the target glycopeptide ion (more exactly, an ion of a glycoform of the glycopeptide).

After the mass-to-charge ratios of a plurality of glycopeptide ions are found in the previously described manner, the quantitative analyzer section determines the relative quantities of the glycoforms of the glycopeptide, using the relative strengths of the peaks corresponding to the glycopeptide ions on the second $MS^1$ spectrum. The structural analyzer section performs de novo sequencing, database search or similar data processing on an $MS^n$ spectrum obtained as a result of an $MS^n$ analysis using each of the aforementioned glycopeptide ions as the precursor ion, to deduce the amino-acid sequence of the peptide and to deduce the structure and composition of the sugar chain included in each glycopeptide as well as its glycosylation site. Thus, the glycopeptide analyzer according to the present invention can perform the relative quantity determination and the structural analysis of the glycoforms of a glycopeptide which has been contained in the sample from the start, and the thereby obtained quantitative information and structural information of the glycoforms can be simultaneously presented to users.

Information obtained by merely performing an $MS^2$ analysis is insufficient for the structural analysis of glycopeptides; normally, either an $MS^3$ analysis or a pseudo $MS^3$ analysis using in-source decay is also necessary. If the time-of-flight mass spectrometer section has the function of performing a TOF/TOF mass spectrometry, it is possible to use the time-of-flight mass spectrometer section only in the $MS^2$ analysis and to use the ion-trap mass spectrometer section in $MS^n$ analyses with n being equal to or greater than three. However, it is common practice to use the ion-trap mass spectrometer section in any $MS^n$ analysis with n being equal to or greater than two.

Advantageous Effects of the Invention

With the glycopeptide analyzer according to the present invention, even if various compounds other than the glycoforms of the target glycopeptide (such as another kind of glycopeptide having a different peptide, a peptide which is not a glycopeptide, or a peptide which has undergone a post-translational modification) are mixed in the sample, the glycoforms of the target glycopeptide can be correctly detected, and the relative quantity determination and the structural analysis of those glycoforms can be performed. Therefore, it is unnecessary to perform a cumbersome pre-treatment of the sample to remove compounds other than the glycoforms of the target glycopeptide. Furthermore, the overall throughput of the structural analysis of the glycoforms is improved, since the $MS^2$ analysis for the structural analysis is not performed on unnecessary precursor ions which have not originated from the target glycopeptide.

DESCRIPTION OF EMBODIMENTS

Figure 1:
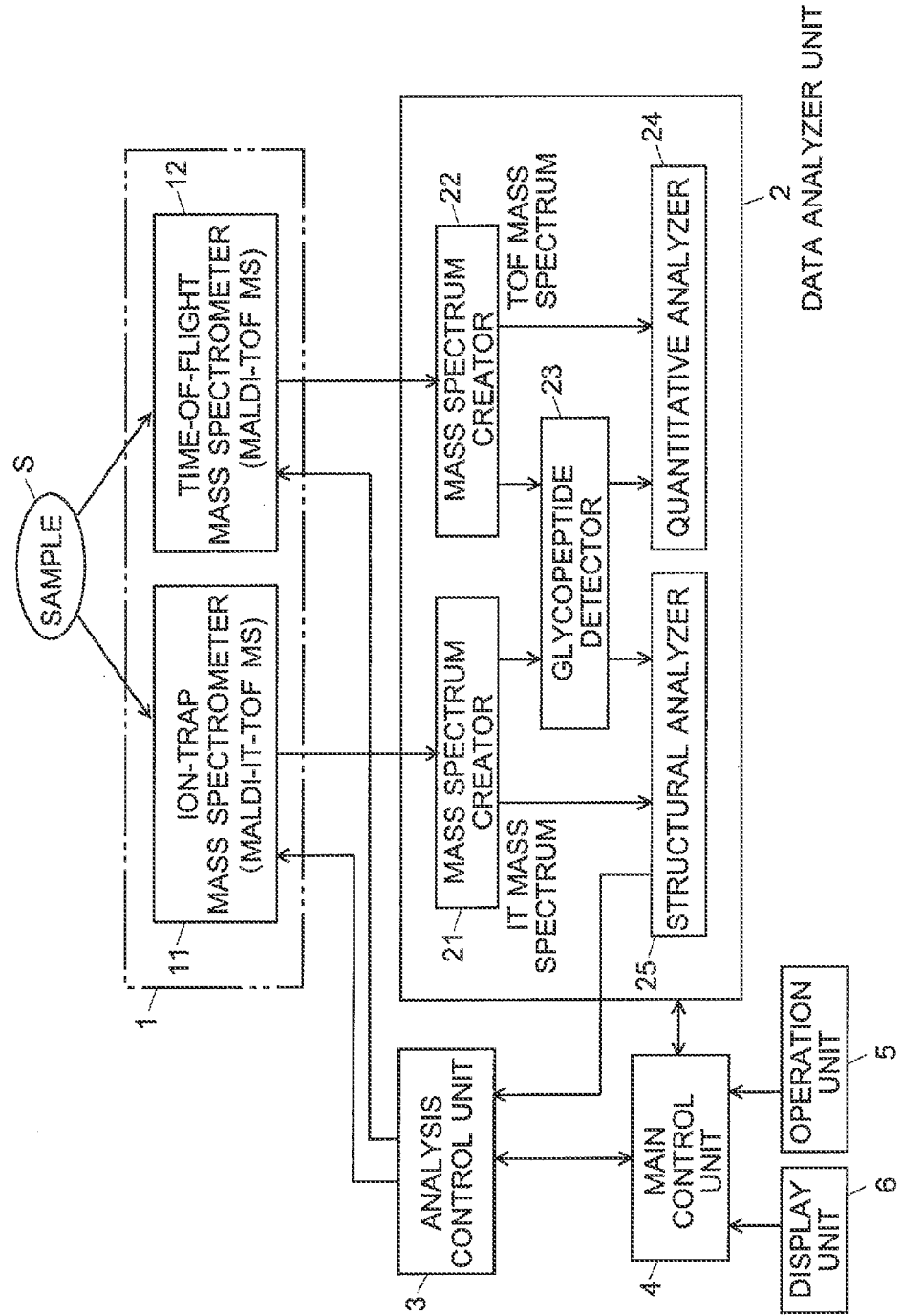
FIG. 1 is a block diagram showing the configuration of the main components of a glycopeptide analyzer as one embodiment of the present invention.

A glycopeptide analyzer as one embodiment of the present invention is hereinafter described in detail with reference to the attached drawings. FIG. 1 is a block diagram showing the configuration of the main components of the glycopeptide analyzer of the present embodiment.

The glycopeptide analyzer of the present embodiment has an analyzer unit 1 for performing an analysis on a sample S and for collecting data, and a data analyzer unit 2 for analyzing and processing the collected data. The analyzer unit 1 includes an ion-trap mass spectrometer section 11 and a time-of-flight mass spectrometer section 12, which are separately used for analyzing samples S containing the same target compound.

Though not shown, the ion-trap mass spectrometer section 11 is a MALDI-IT-TOF mass spectrometer including a MALDI ion source, a three-dimensional quadrupole ion trap, a time-of-flight mass separator and an ion detector. This type of mass spectrometer is capable of performing an $MS^n$ analysis (n is an arbitrary integer equal to or greater than two). That is to say, the ion-trap mass spectrometer section 11 can be operated as follows: In the MALDI ion source, a sample is irradiated with laser light to ionize compounds contained in the sample. The various kinds of ions thereby generated are temporarily captured in the ion trap. In the ion trap, when necessary, an ion having a specific mass-to-charge ratio is selected as a precursor ion, which is subsequently fragmented into product ions by collision induced dissociation (CID). The generated product ions are temporarily captured in the ion trap. Later on, at a preset timing, the product ions are simultaneously ejected from the ion trap and introduced into the time-of-flight mass separator, in which the ions are separated according to their mass-to-charge ratios by being made to fly in a flight space. The separated ions are sequentially detected by the ion detector.

As another example, the ion-trap mass spectrometer section 11 may be a MALDI-IT mass spectrometer which does not have the time-of-flight mass separator but can separate ions according to their mass-to-charge ratios by using a function of the ion trap itself. A Fourier transform mass spectrometer having the function of capturing ions by an electrostatic field and a magnetic field may also be used.

The time-of-flight mass spectrometer section 12 includes a MALDI ion source, a flight space in which ions generated by the ion source and accelerated are made to fly, and an ion detector for detecting the ions which arrives after flying in the flight space. It is typically a linear time-of-flight mass spectrometer having a straight flight space but may also have the function of performing a reflectron TOF/TOF mass spectrometry.

In the time-of-flight mass spectrometer section 12, a sample is irradiated with laser light in the MALDI ion source to ionize compounds in the sample. The various kinds of ions thereby generated are immediately accelerated and introduced into the flight space. Then, the ions are made to fly in the flight space of a predetermined length, whereby the ions are separated according to their mass-to-charge ratios. The separated ions are sequentially detected by the ion detector.

The data analyzer unit 2 includes the following functional blocks: Mass spectrum creators 21 and 22 for creating mass spectra (including MS$^n$ spectra) based on the data respectively obtained in the ion-trap mass spectrometer section 11 and the time-of-flight mass spectrometer section 12; a glycopeptide detector 23 for detecting an ion originating from a target glycopeptide based on the mass spectra; a quantitative analyzer 24 for determining the relative quantities of glycoforms for the detected glycopeptide; and a structural analyzer 25 for analyzing the structure of the glycopeptide by performing various kinds of data processing, such as the deduction of the amino-acid sequence of the peptide, the deduction of the sugar-chain composition, and the identification of the glycosylation site. A configuration with only a single mass spectrum creator is also conceivable, since it is not always necessary to concurrently create the mass spectra based on the data respectively obtained in the ion-trap mass spectrometer section 11 and the time-of-flight mass spectrometer section 12.

The analysis control unit 3 controls the analyzing operations in the ion-trap mass spectrometer section 11 and the time-of-flight mass spectrometer section 12. In particular, it controls the ion-trap mass spectrometer section 11 so as to perform an MS$^n$ analysis with a precursor ion set based on the information obtained in the data processing performed by the structural analyzer 25. The main control unit 4 is responsible for generally controlling the entire system. It also provides a user interface through the operation unit 5 and the display unit 6 connected to it.

At least a portion of the main control unit 4, the analysis control unit 3 and the data analyzer unit 2 can be configured using a personal computer as hardware resources in such a manner that their respective functions are realized by executing a dedicated controlling and processing software program pre-installed on the computer.

One example of the analyzing operation using the glycopeptide analyzer of the present embodiment is hereinafter described with reference to an actual measurement example.

A user sets two samples S containing the same target compound (glycopeptide) prepared for MALDI in the ion-trap mass spectrometer section 11 and the time-of-flight mass spectrometer section 12, respectively. Then, the user performs predetermined operations through the operation unit 5 to set various analysis conditions and then commands the system to initiate the analysis. Upon receiving this command, the analysis control unit 3 makes the ion-trap mass spectrometer section 11 and the time-of-flight mass spectrometer section 12 operate independently so as to perform a mass spectrometry of the set sample S. It should be noted that the mass spectrometry initially performed in the ion-trap mass spectrometer section 11 is an MS$^1$ mass spectrometry, i.e. the normal mass spectrometry in which no CID operation is performed on the ions captured in the ion trap.

As a result of the previously described analysis, an ion intensity signal covering a predetermined time-of-flight range is obtained in each of the ion-trap mass spectrometer section 11 and the time-of-flight mass spectrometer section 12. Each of the mass spectrum creators 21 and 22 receives ion intensity data and performs data processing (e.g. conversion of the time-of-flight values in the data into mass-to-charge ratios) to create a mass spectrum. The two mass spectra are given to the glycopeptide detector 23. For distinction between the two mass spectra, the mass spectrum based on the detection signal obtained in the ion-trap mass spectrometer section 11 is hereinafter called the "IT mass spectrum", while the mass spectrum based on the detection signal obtained in the time-of-flight mass spectrometer section 12 is called the "TOF mass spectrum."

In the ion-trap mass spectrometer section 11, a cooling process for reducing the energy of the ions is performed in the process of capturing ions into the ion trap. The cooling is achieved by introducing a predetermined kind of cooling gas, such as argon gas, into the ion trap and making the oscillating ions come in contact with the cooling gas. In this process, some substance in the sugar chain which is bound to the peptide but is easy to be dissociated (e.g. sialic acid) will be dissociated. As a result, a considerable number of peaks which can be related to neutral loss, i.e. dissociation of the neutral sugar, will be observed on the IT mass spectrum. Since the kinds of substances which become easily dissociated in glycopeptides are commonly known, the glycopeptide detector 23 can detect a group of ion peaks related to neutral loss of known sugars by applying de novo sequencing to the IT mass spectrum. Specifically, this is achieved as follows: After the peaks on the IT mass spectrum are detected and the mass-to-charge ratio of each peak is determined, each pair of the neighboring peaks is checked for whether or not the difference in the mass-to-charge ratio between the two peaks corresponds to the mass of the neutral loss of a known sugar (e.g. sialic acid), and any neighboring peaks whose difference in mass-to-charge ratio corresponds to the mass of the neutral loss of a known sugar are extracted.

The previously described dissociation of a portion of glycan from the glycopeptide ion rarely occurs in the time-of-flight mass spectrometer section 12. Therefore, on the TOF mass spectrum, a peak which corresponds to an ion retaining the intact structure of the glycopeptide (i.e. an intact ion of the glycopeptide) will be observed with high intensity. Accordingly, for example, the glycopeptide detector 23 detects any peak having a strength equal to or higher than a preset threshold on the TOF mass spectrum as a peak that has probably resulted from an intact ion. Subsequently, the glycopeptide detector 23 compares the mass-to-charge ratios of the ions extracted from the IT mass spectrum and those of the ions extracted from the TOF mass spectrum, and detects, as a glycopeptide ion, each ion which has been commonly detected in both mass spectra.

As noted earlier, in the ion-trap mass spectrometer section 11, a portion of the glycan is dissociated in the course of the analysis. The dissociation produces incomplete glycopeptide ions, which appear on the IT mass spectrum being mixed with the ions of glycopeptides (or glycoforms) which have been contained in the sample S from the start and which have the same peptide but different sugar-chain structures. It is impossible to distinguish between the former and latter kinds of ions by the IT mass spectrum only. Meanwhile, the intact ions of the glycopeptides which have been contained in the sample S from the start should appear on the TOF mass spectrum. Therefore, it is possible to deduce, with high reliability, that the ions which commonly appear in both of the IT and TOF mass spectra are the intact ions of glycopeptides which have been contained in the sample S from the start and which have the same peptide, i.e. the intact ions of glycoforms.

Figure 3:
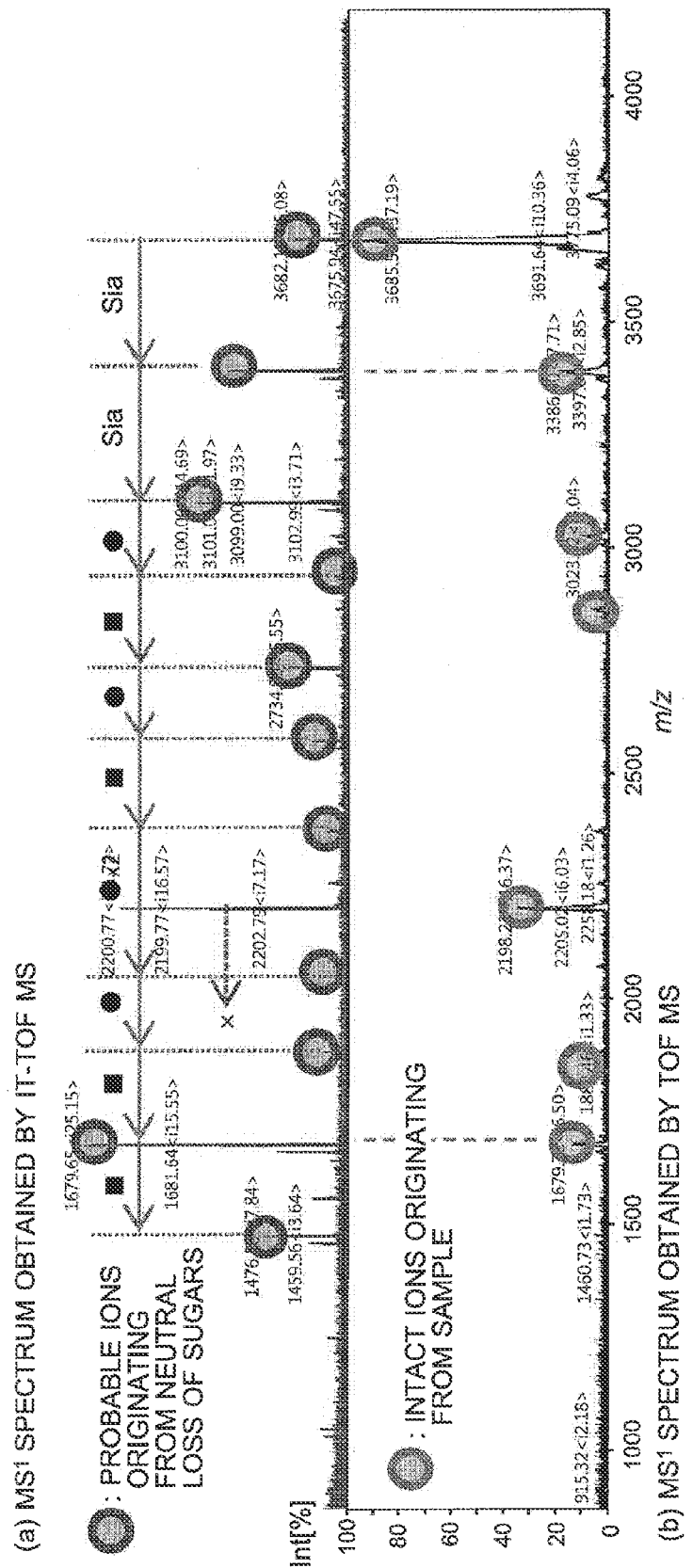
FIG. 3 shows one example of $MS^1$ spectra respectively obtained with the ion-trap mass spectrometer section and the time-of-flight mass spectrometer section in the glycopeptide analyzer of the present embodiment.

FIG. 3(*a*) is an IT-TOF mass spectrum obtained by an actual measurement of a biantennary glycopeptide originating from human transferrin, and FIG. 3(b) is a TOF mass spectrum obtained by an actual measurement of the same sample. The peaks marked with the circles in FIG. 3(a) are the peaks of ions related to neutral loss of sugars by de novo sequencing. It is impossible to determine which of those peaks are the ions corresponding to glycoforms. The peaks marked with the circles in FIG. 3(b) are the peaks which have been detected as intact ions of glycopeptides. It is impossible to distinguish intact ions of the target glycopeptides from those of other kinds of glycopeptides or other kinds of peptides.

Figure 4:
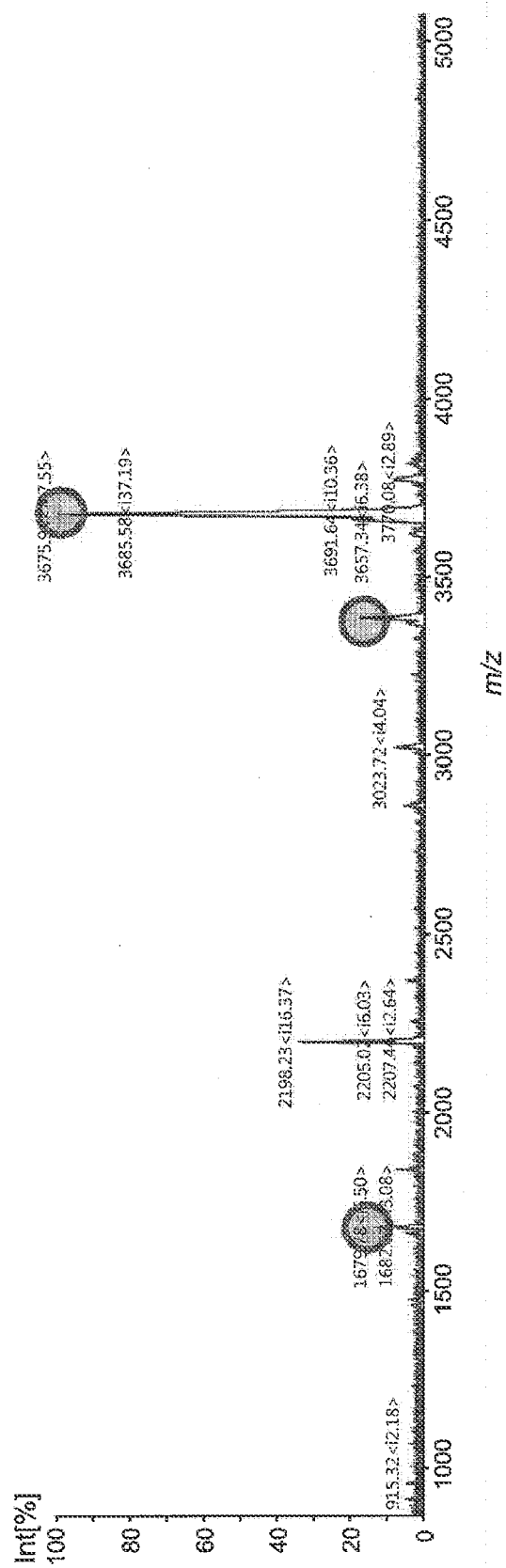
FIG. 4 shows ions originating from a glycopeptide detected based on the $MS^1$ spectra shown in FIG. 3.

FIG. 4 is a TOF mass spectrum showing the result of a search in which the peaks detected in the two mass spectra shown in FIGS. 3(a) and (b) are searched for a peak which commonly appears in both mass spectra within a preset acceptable error tolerance of mass-to-charge ratios. In the present example, three peaks at m/z 1679, m/z 3389 and m/z 3680 have been detected as glycopeptide ions, as marked with the circles in the mass spectrum shown in FIG. 4. It is possible to deduce that those are glycoforms which have the same peptide sequence and merely differ from each other in the structure of the sugar chain binding with the peptide. In other words, the peaks which are not marked with the circles are most likely to be intact ions which are not glycoforms of the target glycopeptide.

For the glycopeptide ions detected by the glycopeptide detector 23, the quantitative analyzer 24 obtains their peak intensities in the TOF mass spectrum obtained by the mass spectrum creator 22 and determines the relative quantities of the glycoforms using the relative values of the peak intensities. Specifically, in the present example, the relative quantities of the glycoforms are calculated from the relative intensities of the three peaks marked with the circles in the mass spectrum shown in FIG. 4. In this calculation, either the peak height or the peak area can be used as the peak intensity.

Figure 2:
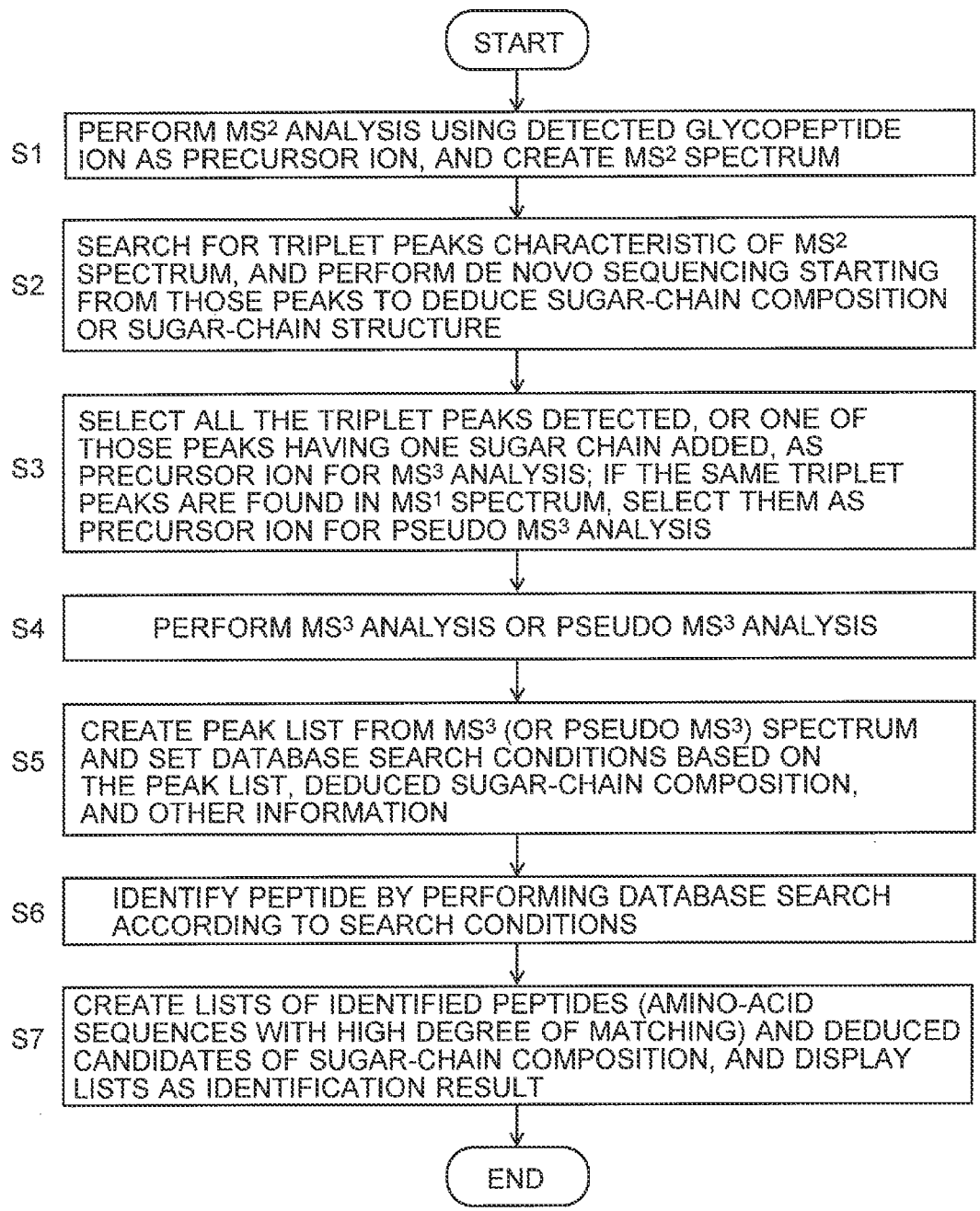
FIG. 2 is a flowchart showing a procedure of the structural analysis of a glycopeptide in the glycopeptide analyzer of the present embodiment.

Meanwhile, for the glycopeptide ions detected by the glycopeptide detector 23, the structural analyzer 25 conducts an $MS^n$ analysis by the ion-trap mass spectrometer section 11 under the control of the analysis control unit 3 and performs a structural analysis of the glycopeptide. The procedure of this structural analysis is hereinafter described with reference to the flowchart shown in FIG. 2.

Initially, the structural analyzer 25 sends information on a glycopeptide ion detected in the previously describes manner to the analysis control unit 3. The analysis control unit 3 controls the operation of the ion-trap mass spectrometer section 11 so as to perform an $MS^2$ analysis of the sample S using the aforementioned ion as the precursor ion. The mass spectrum creator 21 creates an $MS^2$ spectrum based on the detection signal obtained through this $MS^2$ analysis (Step S1). If it is deduced that the glycopeptide ion detected from the mass spectrum contains sialic acid (Sia), an ion from which sialic acids have been completely dissociated by in-source decay or other processes should preferably be selected as the precursor ion for the $MS^2$ analysis.

The structural analyzer 25 searches the obtained $MS^2$ spectrum for triplet peaks which characteristically appear on an $MS^n$ spectrum of N-linked glycopeptides (i.e. three peaks which sequentially appear at intervals of 83 Da and 120 Da in mass-to-charge ratio from lower to higher mass-to-charge ratios). If triplet peaks have been detected, a de novo sequencing which begins with the peak having the highest mass-to-charge ratio in the triplet peaks and terminates at the mass-to-charge ratio of the precursor ion used in the $MS^2$ analysis is performed to deduce a sequence of ion peaks in which the mass-to-charge-ratio difference between every two neighboring peaks corresponds to the mass of the neutral loss of a sugar chain, and to collect information on those peaks as sugar-chain (post-translational modification) information (Step S2). If no triplet peaks have been detected in the $MS^2$ spectrum, the glycopeptide is most likely to be an O-linked glycopeptide. When the sugar-chain composition of this glycopeptide needs to be deduced, the sugar-chain composition deduction should be performed by carrying out the de novo sequencing in descending order of mass-to-charge ratio starting from the precursor ion.

On the assumption that the three kinds of ions corresponding to the triplet peaks detected in Step S2 are, from lower to higher mass-to-charge ratios, 1) a product ion originating from a peptide with all the sugar chains dissociated, 2) a product ion originating from a peptide modified by a cross-ring-cleavage fragment of HexNAc with one sugar chain added, and 3) a product ion originating from a peptide modified by HexNAc, the structural analyzer 25 designates one or more of those product ions as precursor ions for the $MS^3$ analysis and provides the analysis control unit 3 with this information (the designation should minimally include the product ion originating from the peptide modified by HexNAc). Based on this information, the analysis control unit 3 sets the precursor ion for the $MS^3$ analysis. Additionally, if the presence of similar triplet peaks within a preset acceptable error tolerance of mass-to-charge ratios around the aforementioned triplet peaks has been confirmed in the IT mass spectrum, the structural analyzer 25 sets the triplet peaks in the IT mass spectrum (which is an $MS^1$ spectrum) as the precursor ions for the $MS^2$ analysis (Step S3). If the aforementioned characteristic triplet peaks have been located in the IT mass spectrum, it is possible to determine that the glycopeptide ion has been substantially fragmented due to the in-source decay in the MALDI ion source. In this case, the IT mass spectrum can practically be regarded as an $MS^2$ spectrum. Such an $MS^2$ spectrum is hereinafter called the "pseudo" $MS^2$ spectrum, since this spectrum is not the result of an intentional CID operation and should be distinguished from normal $MS^2$ spectra. Similarly, an analysis based on a pseudo $MS^2$ spectrum is hereinafter called the "pseudo" $MS^2$ analysis.

If no triplet peaks have been located in Step S2, it is preferable to select, as the precursor ion for the $MS^3$ analysis, an ion which has been assigned to the lowest mass-to-charge ratio by de novo sequencing performed on the $MS^2$ spectrum. Furthermore, if this precursor ion for the $MS^3$ analysis has also been found in the IT mass spectrum, this ion should preferably be selected as the precursor ion for a pseudo $MS^3$ analysis.

The information about the precursor ions designated in Step S3 is sent to the analysis control unit 3. The analysis control unit 3 controls the operation of the ion-trap mass spectrometer section 11 so as to perform an $MS^3$ analysis or $MS^2$ analysis (pseudo $MS^3$ analysis) on the same sample S. The mass spectrum creator 21 creates an $MS^3$ spectrum or pseudo $MS^3$ spectrum based on the detection signal obtained through the $MS^3$ analysis or pseudo $MS^3$ analysis (Step S4).

From the created $MS^3$ spectrum or pseudo $MS^3$ spectrum, the structural analyzer 25 collects information on significant peaks exclusive of noise peaks or other unwanted components, and creates a peak list. Based on this peak list and the sugar chain (post-translational modification) information deduced in Step S2, the structural analyzer 25 sets search conditions for a database search aimed at peptide identification (Step S5). Specifically, if the presence of a modification by a specific kind of sugar or by a cleavage fragment of a sugar has been revealed by the process in Step S2, that modification can be added to the search conditions as the condition on the post-translational modification. Subsequently, the structural analyzer 25 searches a database (not shown), in which peak patterns of amino-acid sequences of known peptides are stored, to determine the matching of the peak patterns with the above peak list under the above search conditions (Step S6).

When the MS/MS Ions Search included in the Mascot system offered by Matrix Science (a US company) is used as the database search engine, an index ("score") showing the degree of matching of the peak pattern with known peptides is calculated. Based on this information, peptides which have high scores and which are modified in the specified way are selected as candidates of the amino-acid sequence and listed, for example, in descending order of the score. The candidates of the sugar-chain composition deduced by de novo sequencing in Step S2 should also be listed. The obtained lists are displayed as the identification result on the screen of the display unit 6 for presentation to users (Step S7).

It should be noted that the technique for deducing the structure of a glycopeptide detected from mass spectra is not limited to the previously described algorithm. It is possible to appropriately modify the previously described algorithm or adopt a different approach. In any cases, the steps of selecting appropriate precursor ions and performing $MS^n$ analyses are necessary. Minimally, $MS^n$ analyses up to n=3 must be performed. In the case where the time-of-flight mass spectrometer section 12 has the function of performing a reflectron TOF/TOF mass spectrometry, it is possible to perform the $MS^2$ analysis using this function, although the ion-trap mass spectrometer section 11 should always be used for $MS^n$ analyses with n=3 or greater.

Figure 5:
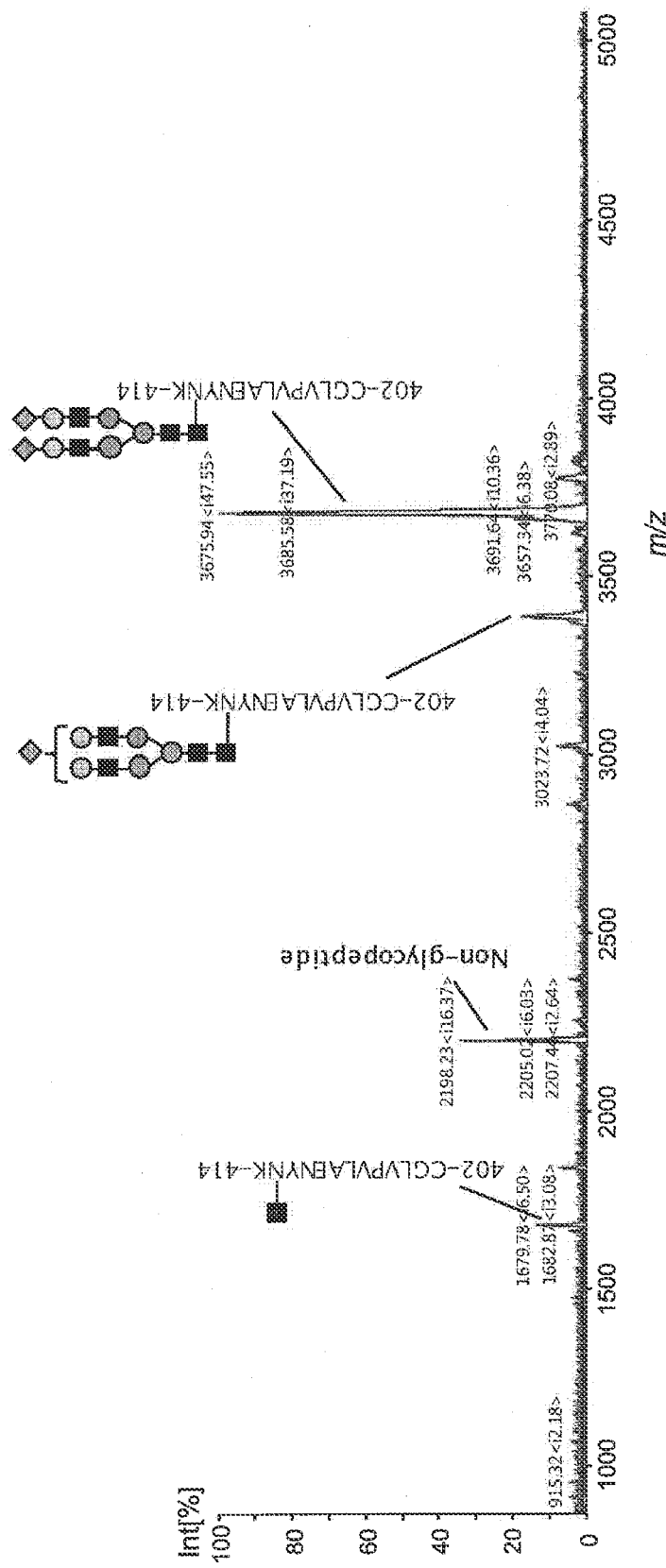
FIG. 5 shows an intensity distribution of glycoforms and the result of a structural analysis obtained in the glycopeptide analyzer of the present embodiment.

FIG. 5 shows one example of displaying the eventually obtained analysis result, in which the result of a structural analysis performed for the glycopeptide ions shown in FIG. 4 according to the previously described process flow is superposed on the mass spectrum. Each of the peaks corresponding to the three glycopeptide ions is linked with the corresponding glycopeptide structure on the display. A peak which has a significant strength but is not a glycoform of the target glycopeptide is annotated as such. Such a display allows users to quickly grasp the structures of the glycoforms contained in the same sample. In the present example, relative intensities are evident from the ratio of the peak intensities, although numerical values of the relative quantities of the glycoforms may additionally be shown on the mass spectrum. For the calculation of the peak-intensity ratio, the peak area may be used as well as the peak height.

In the glycopeptide analyzer of the previously described embodiment, the ion-trap mass spectrometer section 11 and the time-of-flight mass spectrometer section 12 are completely separated from each other. However, since the two modes of measurement do not always need to be simultaneously performed, it is possible to use a hybrid system capable of switching its configuration between a mass spectrometry in which ions are temporarily captured in an ion trap and a mass spectrometry in which the ions extracted from the ion source are directly introduced into a flight space. A specific example available as such a system is the mass spectrometer described in Patent Literature 1. Naturally, when such a hybrid mass spectrometer is adopted, the mass spectrum creators 21 and 22 respectively provided for the two mass spectrometer sections in the previously described embodiment can be integrated into a single unit.

It should be noted that the previously described embodiment is a mere example of the present invention, and any change, modification, addition or the like appropriately made within the spirit of the present invention, other than the already described variations, will naturally fall within the scope of claims of the present patent application.

REFERENCE SIGNS LIST

1 . . . Analyzer Unit
11 . . . Ion-Trap Mass Spectrometer Section
12 . . . Time-of-Flight Mass Spectrometer Section
2 . . . Data Analyzer Unit
21, 22 . . . Mass Spectrum Creator
23 . . . Glycopeptide Detector
24 . . . Quantitative Analyzer
25 . . . Structural Analyzer
3 . . . Analysis Control Unit
4 . . . Main Control Unit
5 . . . Operation Unit
6 . . . Display Unit

The invention claimed is:

1. A glycopeptide analyzer for performing an analysis on a glycoform mixture of a glycoprotein or glycopeptide, comprising:
   a) an ion-trap mass spectrometer section having an ion trap capable of temporarily capturing ions generated from a sample and fragmenting the captured ions, the ion-trap mass spectrometer section being configured to separate the ions according to their mass to charge ratios by the ion trap or another mass separator and to detect the separated ions;
   b) a time-of-flight mass spectrometer section for introducing ions generated from a sample into a flight space, for separating the ions according to their mass-to-charge ratios within the flight space, and for detecting the separated ions;
   c) a glycopeptide detector section for detecting peaks related to dissociation of a portion or the entirety of glycan on a first $MS^1$ spectrum created based on a result of a measurement by the ion-trap mass spectrometer section, for detecting molecular ion peaks on a second $MS^1$ spectrum created based on a result of a measurement by the time-of-flight mass spectrometer section, and for finding glycopeptide ions from common peaks located on both $MS^1$ spectra;
   d) a quantitative analyzer section for determining, for the glycopeptide ion detected by the glycopeptide detector section, a relative quantity of a glycoform using a relative peak intensity on the second $MS^2$ spectrum; and
   e) a structural analyzer section for performing, for the glycopeptide ion detected by the glycopeptide detector section, a structural analysis of a glycoform using, at least, the result of an $MS^n$ analysis (where n is an integer equal to or greater than two) performed by the ion-trap mass spectrometer section.

2. The glycopeptide analyzer according to claim 1, wherein:
   the ion-trap mass spectrometer section is a matrix-assisted laser desorption ionization ion-trap time-of-flight mass spectrometer, and the time-of-flight mass spectrometer section is a matrix-assisted laser desorption ionization liner time-of-flight mass spectrometer.

3. The glycopeptide analyzer according to claim 1, wherein:
   the glycopeptide detector section analyzes the first $MS^1$ spectrum by de novo sequencing to detect each peak which is likely to be a fragment ion of glycopeptide ion from which a portion or the entirety of glycan has been dissociated as a neutral loss.

4. The glycopeptide analyzer according to claim 1, wherein:
the glycopeptide detector section detects each significant peak which is located on the second $MS^1$ spectrum and whose signal intensity exceeds a threshold, on an assumption that such a peak corresponds to an ion originating from an intact molecule.

\* \* \* \* \*